(12) United States Patent
Takagi et al.

(10) Patent No.: US 9,842,393 B2
(45) Date of Patent: Dec. 12, 2017

(54) CELL EVALUATION METHOD

(71) Applicant: OLYMPUS CORPORATION, Hachioji-shi, Tokyo (JP)

(72) Inventors: Kosuke Takagi, Tokyo (JP); Yoshihiro Shimada, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 93 days.

(21) Appl. No.: 15/166,195

(22) Filed: May 26, 2016

(65) Prior Publication Data

US 2016/0350915 A1    Dec. 1, 2016

(30) Foreign Application Priority Data

May 29, 2015  (JP) ................................. 2015-110116

(51) Int. Cl.
| | |
|---|---|
| *G06T 7/00* | (2017.01) |
| *G01N 33/483* | (2006.01) |
| *G06K 9/52* | (2006.01) |
| *G06T 7/70* | (2017.01) |
| *G06T 7/66* | (2017.01) |
| *G06K 9/00* | (2006.01) |

(52) U.S. Cl.
CPC ....... *G06T 7/0012* (2013.01); *G01N 33/4833* (2013.01); *G06K 9/0014* (2013.01); *G06K 9/52* (2013.01); *G06T 7/66* (2017.01); *G06T 7/70* (2017.01); *G06T 2200/04* (2013.01); *G06T 2207/30004* (2013.01)

(58) Field of Classification Search
CPC .... G01N 33/4833; G06K 9/0014; G06K 9/52; G06T 7/0012; G06T 7/66; G06T 2200/04; G06T 2207/30004; G06T 2207/30024
See application file for complete search history.

(56) References Cited

U.S. PATENT DOCUMENTS

| | | | | |
|---|---|---|---|---|
| 5,737,250 | A * | 4/1998 | Sawahata | ............ G06F 17/5018 345/419 |
| 2009/0213214 | A1* | 8/2009 | Yamada | ............. G01N 21/6458 348/80 |
| 2012/0243767 | A1* | 9/2012 | Nakano | ................. G06K 9/0014 382/133 |
| 2014/0147837 | A1* | 5/2014 | Kimura | .............. G01N 15/1459 435/6.1 |

(Continued)

FOREIGN PATENT DOCUMENTS

JP    2014149235 A    8/2014

*Primary Examiner* — Edward Park
(74) *Attorney, Agent, or Firm* — Holtz, Holtz & Volek PC

(57) ABSTRACT

A cell evaluation method includes: a labeling step of labeling at least some of cells constituting a cell clump with a chemical substance; an image-capturing step of acquiring a plurality of slice images of the labeled cells, for at least part of the cell clump; an evaluating step of evaluating the characteristics of the cells on the basis of the plurality of slice images; a 3D-image creating step of creating a 3D image of at least part of the cell clump by subjecting the plurality of slice images to image processing; a center-of-gravity determining step of determining, from the 3D image, a center-of-gravity position of the cell clump; and an organizing step of organizing evaluation results obtained in the evaluating step, with respect to the distance from the center-of-gravity position.

17 Claims, 5 Drawing Sheets

(56) References Cited

U.S. PATENT DOCUMENTS

| | | | |
|---|---|---|---|
| 2014/0220592 A1 | 8/2014 | Fujimoto et al. | |
| 2014/0270457 A1* | 9/2014 | Bhargava | G06K 9/0014 |
| | | | 382/133 |
| 2016/0350915 A1* | 12/2016 | Takagi | G06T 7/0012 |

* cited by examiner

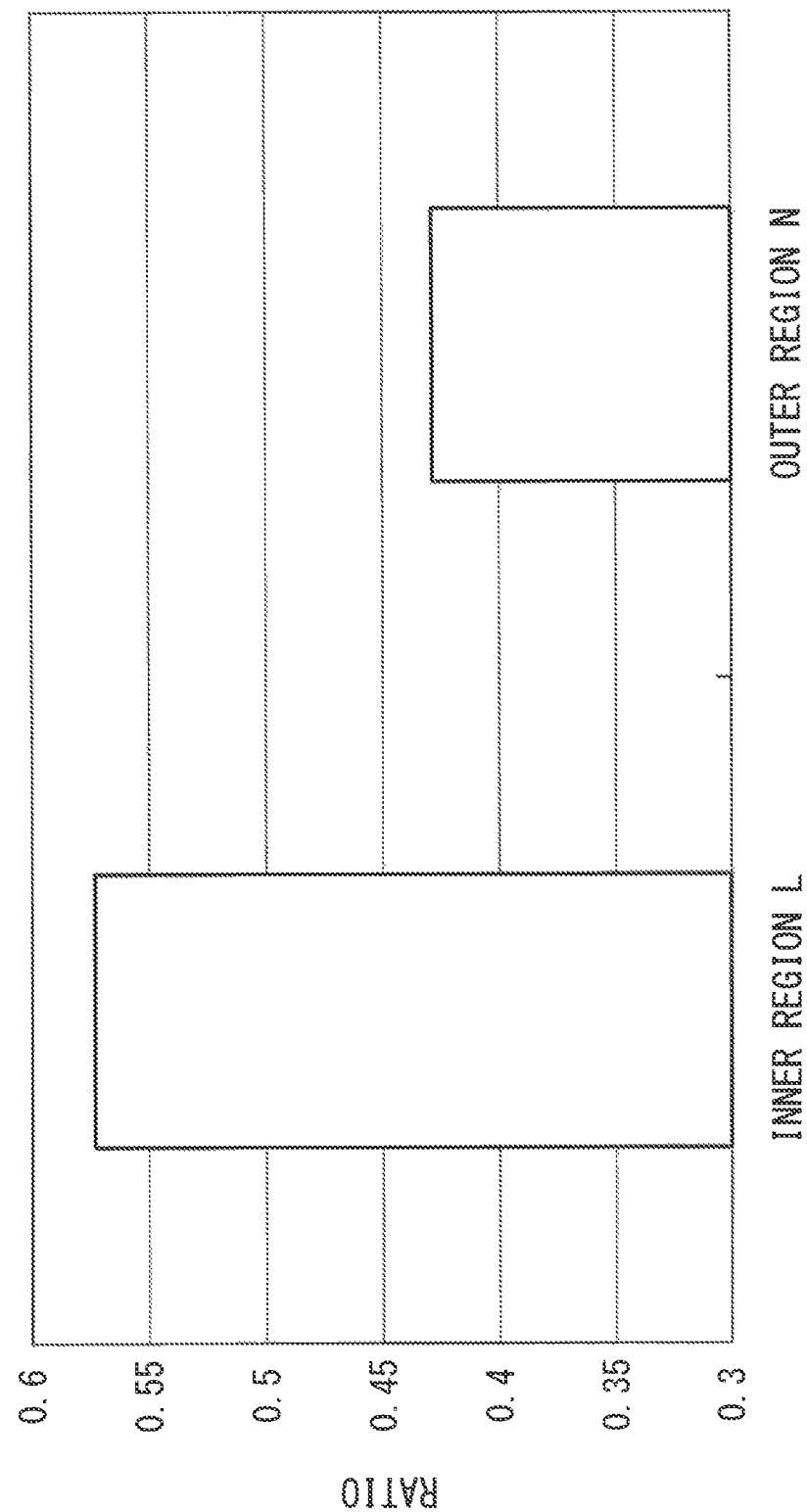

CELL EVALUATION METHOD

CROSS-REFERENCE TO RELATED APPLICATIONS

This application is based on Japanese Patent Application No. 2015-110116, filed on May 29, 2015, the content of which is incorporated herein by reference.

TECHNICAL FIELD

The present invention relates to a cell evaluation method.

BACKGROUND ART

In order to check the effectiveness of medicine in an environment close to that in the living body, three-dimensional culturing, in which cells are cultured in three dimensions, has been conventionally performed. In such three-dimensional culturing, there is a known calibration method in which, in order to observe the culture conditions of a cell clump in which a plurality of cells are aggregated in three dimensions, the accuracy of estimating the volume of the cell clump from an image including the cell clump is improved (for example, see PTL 1).

The technique in PTL 1 is used to analyze the whole cell clump but is not used to analyze individual cells constituting the cell clump. In cell-based studies or drug screening, it is necessary to quantify the reactions of individual cells constituting a cell clump. In particular, among the cells constituting the cell clump, the reactions are different between inner-side cells and outer-side cells.

CITATION LIST

Patent Literature

{PTL 1} Japanese Unexamined Patent Application, Publication No. 2014-149235

SUMMARY OF INVENTION

According to one aspect, the present invention provides a cell evaluation method including: a labeling step of labeling at least some of cells constituting a cell clump with at least one chemical substance that produces fluorescence or luminescence; an image-capturing step of acquiring a plurality of slice images of the cells that are labeled in the labeling step, for at least part of the cell clump; an evaluating step of evaluating the characteristics of the cells on the basis of the plurality of slice images acquired in the image-capturing step; a 3D-image creating step of creating a 3D image of at least part of the cell clump by subjecting the plurality of slice images acquired in the image-capturing step to image processing; a center-of-gravity determining step of determining a center-of-gravity position of the cell clump from the 3D image of the cell clump created in the 3D-image creating step; and an organizing step of organizing evaluation results obtained in the evaluating step, with respect to the distance from the center-of-gravity position determined in the center-of-gravity determining step.

BRIEF DESCRIPTION OF DRAWINGS

FIG. 6 is a graph showing example evaluation results obtained by the cell evaluation method shown in FIG. 1.

DESCRIPTION OF EMBODIMENTS

A cell evaluation method according to one embodiment of the present invention will be described below with reference to the drawings.

Figure 1:
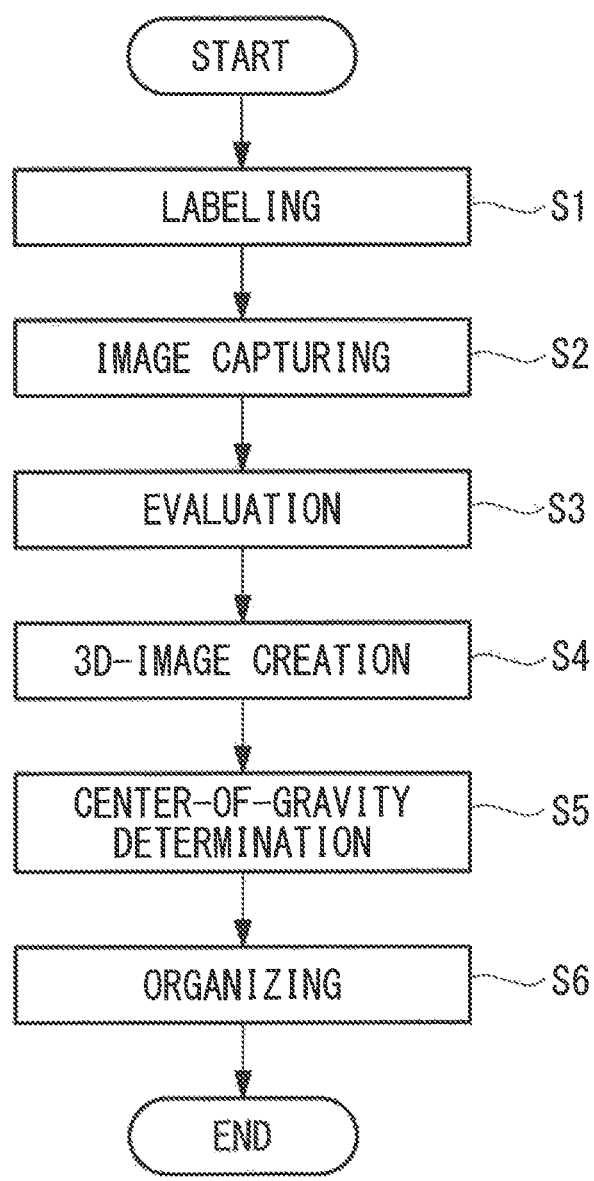
FIG. 1 is a flowchart showing a cell evaluation method according to one embodiment of the present invention.

As shown in FIG. 1, the cell evaluation method of this embodiment includes: a labeling step S1 of labeling cells Y constituting a cell clump X with a chemical substance; an image-capturing step S2 of acquiring a plurality of slice images of the labeled cells Y; an evaluating step S3 of evaluating the characteristics of the cells Y on the basis of the plurality of acquired slice images; a 3D-image creating step S4 of creating a 3D image of the cell clump X from the plurality of slice images; a center-of-gravity determining step S5 of determining a center-of-gravity position O of the cell clump X from the created 3D image; and an organizing step S6 of organizing evaluation results in relation to the distances from the determined center-of-gravity position O.

The cell evaluation method of this embodiment is performed by using a microscope system 1 to be described below.

Figure 2:
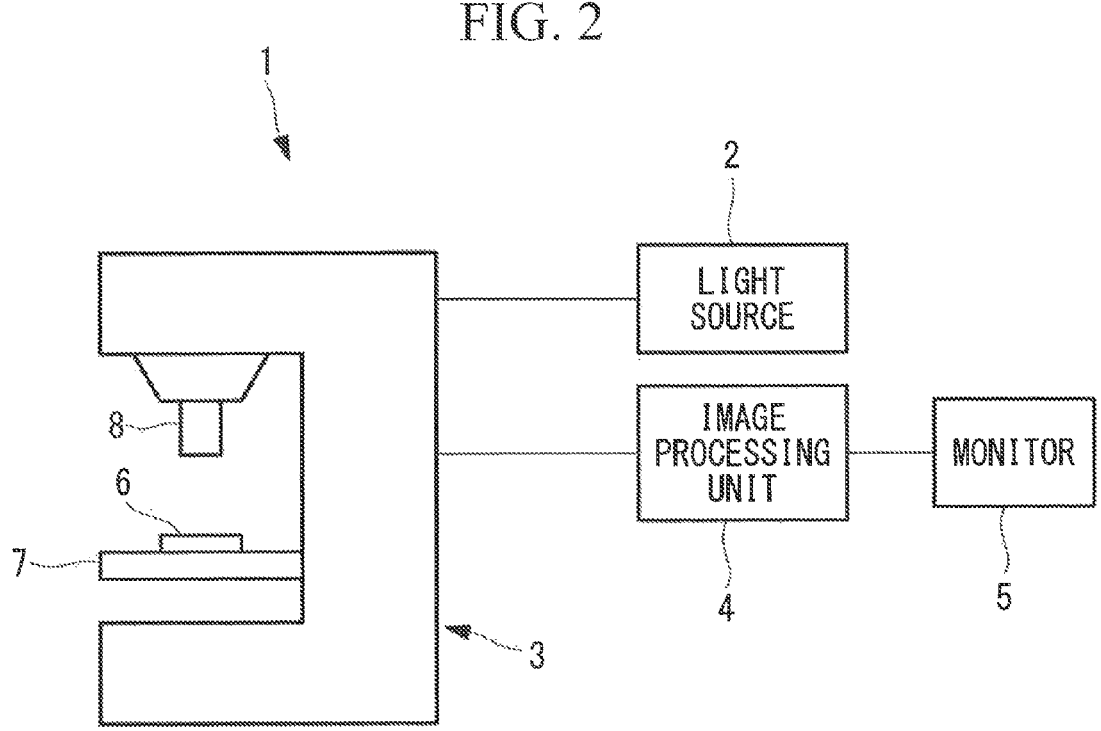
FIG. 2 is a diagram showing a microscope system used to perform the cell evaluation method shown in FIG. 1.

As shown in FIG. 2, the microscope system 1 is provided with a light source 2 that produces illumination light, a microscope 3 that radiates the illumination light onto the cell clump X and that captures an image of the cell clump X, an image processing unit 4 that processes an acquired slice image, and a monitor 5 that displays the processed result.

In the labeling step S1, a chemical substance, such as a fluorescent dye or a fluorescent protein, is supplied to the cell clump X, thereby labeling a specific component in cells. The components in a cell include a cell nucleus, a cell membrane, cell cytoplasm, a particular organ such as mitochondria, DNA, RNA, and so forth.

The cell clump X means the aggregation or the clump of the cells Y, which has a 3D structure. Examples of the cell clump X include spheroid, sphere, colony, EB (embryoid body), and organoid.

As shown in FIG. 2, the image-capturing step S2 is performed by the microscope 3, which acquires a slice image of a sample formed of the cell clump X.

As shown in FIG. 2, the microscope 3 is, for example, a laser-scanning confocal microscope and is provided with a stage 7 on which a container 6 accommodating the sample is mounted and that three-dimensionally moves the container 6 and an objective lens 8 that is disposed above the stage 7. For example, it is possible to adopt, as the container 6, a microscope-observation container, such as a multiwell, a dish, or a slide, or another special container.

In the image-capturing step S2, while moving the stage 7 three-dimensionally with respect to the objective lens 8, thereby moving the cell clump X three-dimensionally with respect to the focal position of the objective lens 8, laser light is scanned at each position, a slice image of a cell Y that is located at the focal position is acquired, and thus a plurality of slice images of each cell Y are acquired.

The evaluating step S3, the 3D-image creating step S4, the center-of-gravity determining step S5, and the organizing step S6 are performed by the image processing unit 4.

In the evaluating step S3, the characteristics of the cells Y are evaluated according to the type of chemical substance supplied in the labeling step S1, on the basis of the slice images acquired in the image-capturing step S2. For example, in a case of immunostaining, whether or not the cells Y are stained with a particular fluorescent dye is evaluated. In a case in which a fluorescent protein, such as GFP, is supplied, whether or not the cells Y give a particular reaction is evaluated. In a case in which an indicator, such as Fucci, is supplied, the phase of the cells Y in the cell cycle is evaluated.

Figure 3:
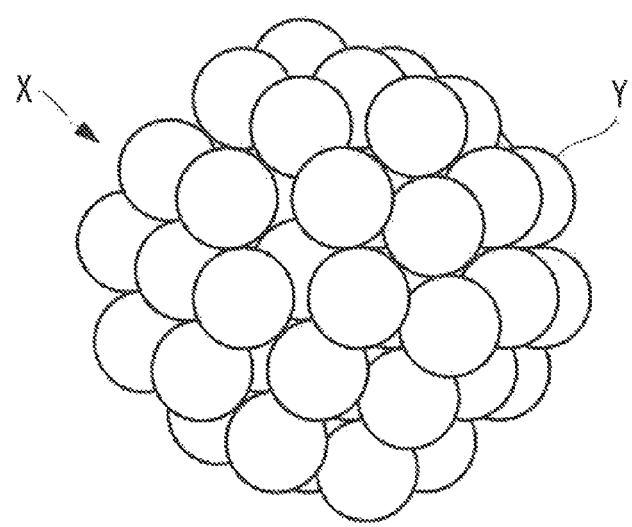
FIG. 3 is a view showing an example 3D image of a cell clump, created in a 3D-image creating step of the cell evaluation method shown in FIG. 1.

In the 3D-image creating step S4, the plurality of slice images of each cell Y, which are acquired in the image-capturing step S2, are subjected to image processing, thereby creating a 3D image of the whole cell clump X, as shown in FIG. 3.

Figure 4:
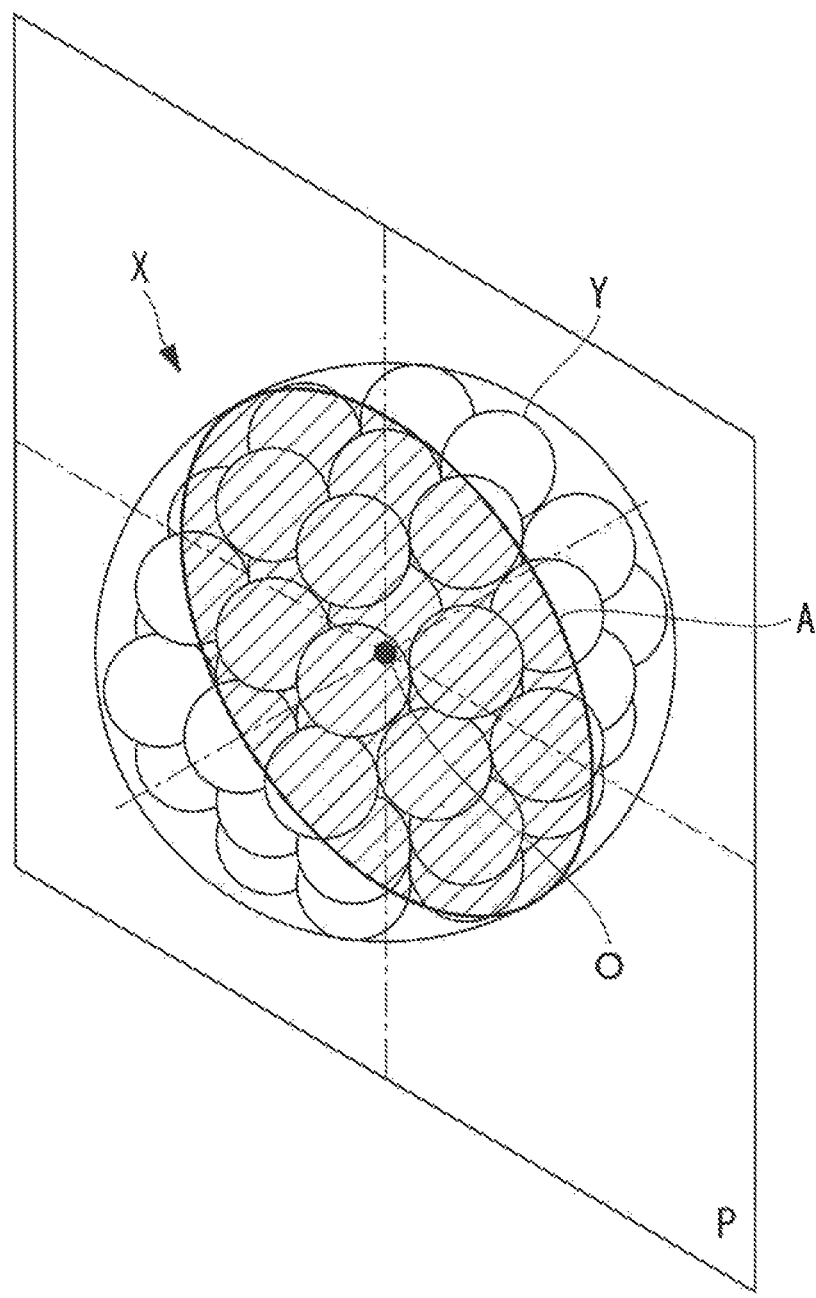
FIG. 4 is a view for explaining a method of determining the center of gravity of the cell clump in a center-of-gravity determining step of the cell evaluation method shown in FIG. 1.

In the center-of-gravity determining step S5, for example, as shown in FIG. 4, the 3D image of the whole cell clump X, which is created in the 3D-image creating step S4, is sliced along a plurality of planes P parallel to each other in a particular direction, cross sections A of the cell clump X in the planes P are compared to extract the cross section A that has the maximum area, and the center-of-gravity position O in the extracted cross section A is obtained, thus determining the center-of-gravity position O of the cell clump X.

In the organizing step S6, the results of the characteristic evaluation performed in the evaluating step S3 are organized on the basis of the distances from the center-of-gravity position O determined in the center-of-gravity determining step S5.

Figure 5:
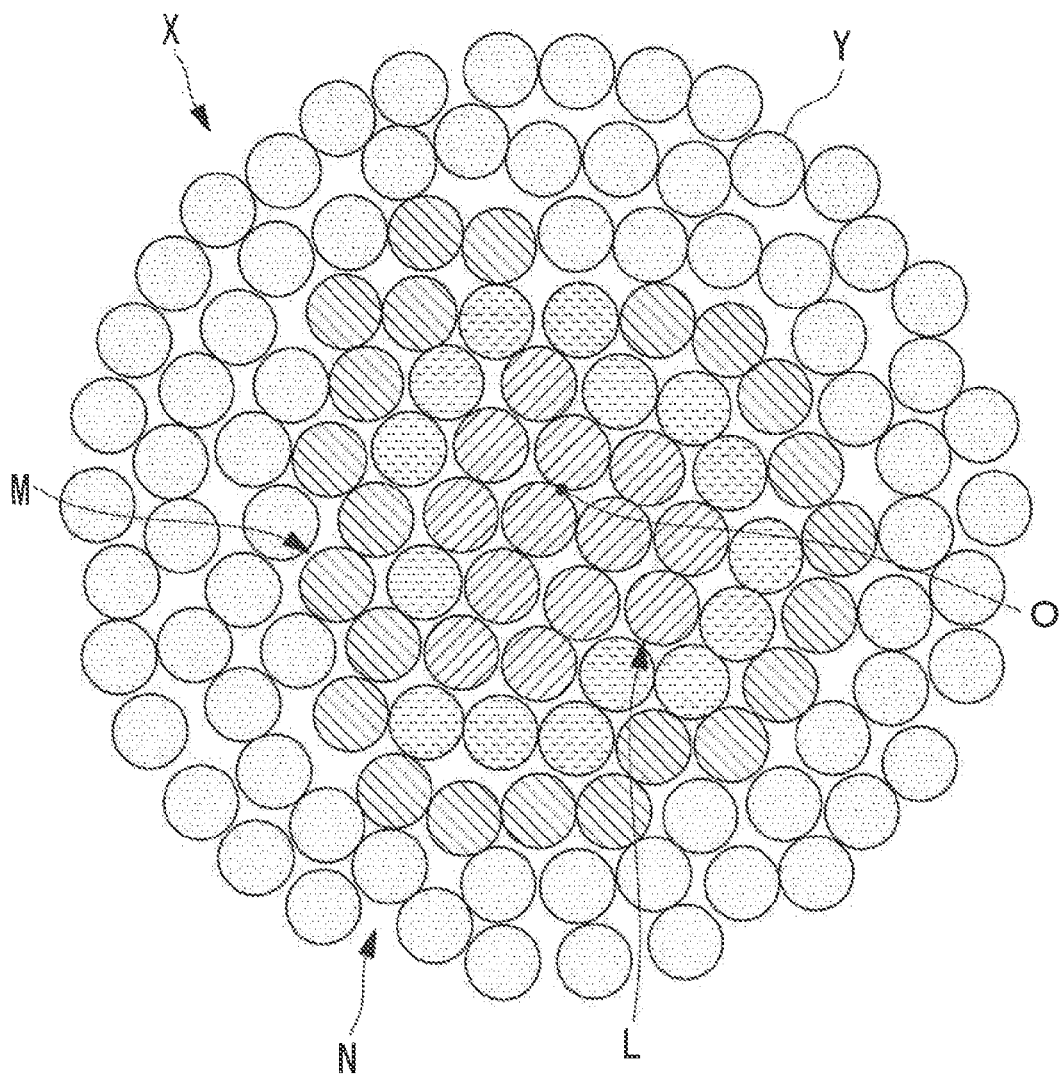
FIG. 5 is a view schematically showing a cross section of the 3D image of the cell clump, created by the cell evaluation method shown in FIG. 1.

Specifically, as shown in FIG. 5, when a cross section of the cell clump X is obtained, an inner region L, an intermediate region M, and an outer region N exhibit different reactions to the chemical substance, in some cases. The inner region L is a region close to the center-of-gravity position O. The intermediate region M is a region located at an outer side of the inner region L. The outer region N is a region located at an outer side of the intermediate region M. For example, as the distance to the vicinity of the center-of-gravity position O of the cell clump X is reduced, a hypoxic condition is produced because contact with the external environment is blocked by the surrounding cells Y, and thus cell division hardly occurs.

In the organizing step S6, the whole cell clump X is divided into the regions L, M, and N according to the distance from the center-of-gravity position O, and the characteristics of the cells Y are organized for each of the regions L, M, and N. For example, a chemical substance that produces fluorescence of different colors (such as green and red) according to the characteristics of the cells Y is administered in the labeling step S1, the color of each of the cells Y is evaluated in the evaluating step S3, and, in the organizing step S6, the ratio of the number of red cells Y and the number of green cells Y in each of the inner region L and the outer region N is calculated and is shown in a graph for each of the regions L and N, as in FIG. 6.

According to the thus-configured cell evaluation method of this embodiment, there is an advantage that it is possible to evaluate the characteristics of, not the cell clump X as a whole, but individual cells Y constituting the cell clump X, according to the location in the cell clump X. The cell clump X itself is the aggregation of the cells Y existing in a condition close to an in-vivo condition, and thus it is possible to get an accurate evaluation close to a clinical evaluation, compared with a method in which a single cell Y is cultured or a method in which a cell Y is cultured while in contact with the container 6.

Therefore, according to the cell evaluation method of this embodiment, there is an advantage that, in cell-Y based studies or in drug screening, a change in the characteristics of the individual cells Y can be quantitatively evaluated in a condition close to an in-vivo condition.

In this embodiment, the results from evaluation of the characteristics of the cells Y are organized according to the distance from the center-of-gravity position O of the cell clump X; however, instead of this, the results may be organized according to the distance from the center-of-gravity position O in the direction of the gravitational force.

For example, when a chemical substance is supplied to the cell clump X for drug screening, cells Y that are located lower are more affected by the gravitational force. Therefore, by organizing the evaluation results according to the distance in the direction of the gravitational force, the effectiveness of the chemical substance can be accurately evaluated.

In this embodiment, a description has been given of an example case in which a chemical substance, such as a fluorescent dye or a fluorescent protein, is supplied to the cell clump X; however, instead of this, a chemical substance that produces luminescence may be used to perform the labeling step S1.

In this embodiment, a description has been given of an example case in which a laser-scanning confocal microscope is used; however, instead of this, it is possible to use, to perform the image-capturing step S2, any microscope that can acquire slice images of cells Y constituting the cell clump X, such as a laser-scanning multiphoton excitation microscope or a light-sheet microscope.

In this embodiment, the center-of-gravity position O of the cell clump X is obtained from the center-of-gravity position O of a cross section A that has the maximum cross-sectional area in a particular direction, by using the 3D image of the cell clump X; however, instead of this, the center-of-gravity position O may be estimated from the location of each cell Y constituting the cell clump X.

In this embodiment, although the color of each cell Y is evaluated, instead of this, the quantity of fluorescence in each cell nucleus may be evaluated.

In this embodiment, although the cells Y constituting the cell clump X are extracted, instead of this, the number of cell nuclei may be counted for each of the regions L, M, and N, or the density of the cells Y may be calculated for each of the regions L, M, and N. Furthermore, the cell cytoplasm may be used instead of the cell nucleus. Furthermore, it is also possible to supply, to the cell clump X, a first chemical substance that specifically labels cell nuclei and a second chemical substance that specifically labels cell nuclei of dead cells, and to evaluate the ratio of the dead cells for each of the regions L, M, and N.

It is also possible to supply, to the cell clump X, a fluorescent protein whose fluorescence wavelength changes according to the phases of the cell cycle, to make it express, and to evaluate the ratio of the respective phases of the cell cycle for each of the regions L, M, and N by using the wavelength of fluorescence producing color according to the phase of the cell cycle.

It is also possible to supply a chemical substance that specifically labels cell nuclei and micronuclei, to create a 3D image of the cell nuclei and the micronuclei from acquired slice images, to extract only micronuclei whose volumes are less than a predetermined threshold, and to evaluate the ratio of the occurrence of the micronuclei for each of the regions L, M, and N.

It is also possible to extract fragmented cell nuclei according to the volume and to evaluate the ratio of fragmentation of the cell nuclei for each of the regions L, M, and N.

It is also possible to supply a chemical substance that specifically labels cell membranes, to create a 3D image of the cell membranes, and to calculate the volume in the cell membranes, thereby evaluating the volume of the cells Y for each of the regions L, M, and N.

The following aspect of the invention is derived from the above-described embodiment.

According to one aspect, the present invention provides a cell evaluation method including: a labeling step of labeling at least some of cells constituting a cell clump with at least one chemical substance that produces fluorescence or luminescence; an image-capturing step of acquiring a plurality of slice images of the cells that are labeled in the labeling step, for at least part of the cell clump; an evaluating step of evaluating the characteristics of the cells on the basis of the plurality of slice images acquired in the image-capturing step; a 3D-image creating step of creating a 3D image of at least part of the cell clump by subjecting the plurality of slice images acquired in the image-capturing step to image processing; a center-of-gravity determining step of determining a center-of-gravity position of the cell clump from the 3D image of the cell clump created in the 3D-image creating step; and an organizing step of organizing evaluation results obtained in the evaluating step, with respect to the distance from the center-of-gravity position determined in the center-of-gravity determining step.

According to this aspect, a plurality of slice images of cells are acquired, in the image-capturing step, for at least part of the cell clump in which at least some of the cells are labeled with the chemical substance in the labeling step, and the characteristics of the cells are evaluated, in the evaluating step, on the basis of the acquired slice images. Furthermore, in the 3D-image creating step, a 3D image is created by subjecting the plurality of slice images to image processing, and, in the center-of-gravity determining step, the center-of-gravity position of the cell clump is determined. Then, in the organizing step, the characteristics-evaluation results obtained in the evaluating step are organized with respect to the distance from the center-of-gravity position. Thus, it is possible to evaluate cells cultured in the form of a cell clump, which is close to the form in the living body, in association with the location in the cell clump.

In the above-described aspect, in the organizing step, the evaluation results may be organized with respect to the distance in the direction of gravitational force from the center-of-gravity position determined in the center-of-gravity determining step.

By doing so, it is possible to evaluate a difference in evaluation according to the location, in the direction of gravitational force, of each cell existing in the cell clump.

In the above-described aspect, in the organizing step, at least part of the cell clump may be divided into a plurality of regions according to the distance from the center-of-gravity position determined in the center-of-gravity determining step, and the evaluation results of the cells existing in each of the regions may be organized for the region.

By doing so, it is possible to evaluate each cell separately for each of an outer region of the cell clump that is in contact with an external environment and an inner region thereof that is not in contact with the external environment.

In the above-described aspect, in the evaluating step, the amount of light produced in each of the cells may be evaluated.

By doing so, it is possible to evaluate, from the difference in light level, the difference in the characteristics of the cells according to the location in the cell clump.

In the above-described aspect, in the evaluating step, the number of components detected in the cells may be evaluated.

In the above-described aspect, in the evaluating step, the density of components detected in the cells may be evaluated.

In the above-described aspect, the components may be cell nuclei.

In the above-described aspect, in the labeling step, a first chemical substance that can specifically label cell nuclei and a second chemical substance that can specifically label cell nuclei of dead cells and that produces light having a different wavelength from that produced by the first chemical substance may be used to label the cell nuclei; and in the evaluating step, the ratio of the dead cells may be evaluated.

In the above-described aspect, in the labeling step, a fluorescent protein whose fluorescence wavelength changes according to a phase of a cell cycle may be used to label the cells; and in the evaluating step, the ratio of the phase of the cell cycle may be evaluated.

In the above-described aspect, components detected in each of the cells may be cell cytoplasm.

In the above-described aspect, in the labeling step, a chemical substance that can specifically label cell nuclei may be used to label the cell nuclei; and in the evaluating step, only micronuclei that have volumes less than a predetermined threshold may be extracted from a 3D image of cell nuclei and the micronuclei, acquired in the 3D-image creating step, and the incidence of the micronuclei may be evaluated.

In the above-described aspect, in the labeling step, a chemical substance that can specifically label cell nuclei may be used to label the cell nuclei; in the evaluating step, fragmented cell nuclei that have volumes less than a predetermined threshold may be extracted from a 3D image of the fragmented cell nuclei acquired in the 3D-image creating step, and the fragmentation percentage of the cell nuclei may be evaluated.

In the above-described aspect, in the labeling step, a chemical substance that can specifically label cell membranes may be used to label the cell membranes; and in the evaluating step, the internal volume of cell membranes may be calculated from a 3D image of the cell membranes that is acquired in the 3D-image creating step, thereby evaluating the volume of the cells.

In the above-described aspect, in the center-of-gravity determining step, the center-of-gravity position may be determined on the basis of, among cross sections of a 3D image of the whole cell clump along a plurality of planes parallel to each other, a cross section of the cell clump in the plane that has the maximum cross-section area of the cell clump.

In the above-described aspect, in the center-of-gravity determining step, the center-of-gravity position of the cell clump may be estimated on the basis of the distribution of components of each of the cells in the 3D image.

REFERENCE SIGNS LIST

S1 labeling step
S2 image-capturing step
S3 evaluating step
S4 3D-image creating step
S5 center-of-gravity determining step
S6 organizing step
L inner region (region)
M intermediate region (region)
N outer region (region)
O center-of-gravity position
X cell clump
Y cell

The invention claimed is:

1. A cell evaluation method comprising:
 a labeling step of labeling at least some of cells constituting a cell clump with at least one chemical substance that produces fluorescence or luminescence;
 an image-capturing step of acquiring a plurality of slice images of the cells that are labeled in the labeling step, for at least part of the cell clump;
 an evaluating step of evaluating the characteristics of the cells on the basis of the plurality of slice images acquired in the image-capturing step;
 a 3D-image creating step of creating a 3D image of at least part of the cell clump by subjecting the plurality of slice images acquired in the image-capturing step to image processing;
 a center-of-gravity determining step of determining a center-of-gravity position of the cell clump from the 3D image of the cell clump created in the 3D-image creating step; and
 an organizing step of organizing evaluation results obtained in the evaluating step, with respect to the distance from the center-of-gravity position determined in the center-of-gravity determining step.

2. The cell evaluation method according to claim 1, wherein, in the organizing step, the evaluation results are organized with respect to the distance in a direction of gravitational force from the center-of-gravity position determined in the center-of-gravity determining step.

3. The cell evaluation method according to claim 1, wherein, in the organizing step, at least part of the cell clump is divided into a plurality of regions according to the distance from the center-of-gravity position determined in the center-of-gravity determining step, and the evaluation results of the cells existing in each of the regions are organized for the region.

4. The cell evaluation method according to claim 1, wherein, in the evaluating step, the amount of light produced in components detected in each of the cells is evaluated.

5. The cell evaluation method according to claim 4, wherein the components are cell nuclei.

6. The cell evaluation method according to claim 1, wherein, in the evaluating step, the number of components detected in the cells is evaluated.

7. The cell evaluation method according to claim 6, wherein the components are cell nuclei.

8. The cell evaluation method according to claim 1, wherein, in the evaluating step, the density of components detected in the cells is evaluated.

9. The cell evaluation method according to claim 8, wherein the components are cell nuclei.

10. The cell evaluation method according to claim 1,
 wherein, in the labeling step, a first chemical substance that can specifically label cell nuclei and a second chemical substance that can specifically label cell nuclei of dead cells and that produces light having a different wavelength from that produced by the first chemical substance are used to label the cell nuclei; and
 in the evaluating step, the ratio of the dead cells is evaluated.

11. The cell evaluation method according to claim 1,
 wherein, in the labeling step, a fluorescent protein whose fluorescence wavelength changes according to a phase of a cell cycle is used to label the cells; and
 in the evaluating step, the ratio of the phase of the cell cycle is evaluated.

12. The cell evaluation method according to claim 1, wherein components detected in each of the cells are cell cytoplasm.

13. The cell evaluation method according to claim 1,
 wherein, in the labeling step, a chemical substance that can specifically label cell nuclei is used to label the cell nuclei; and
 in the evaluating step, only micronuclei that have volumes less than a predetermined threshold are extracted from a 3D image of cell nuclei and the micronuclei, acquired in the 3D-image creating step, and an incidence of the micronuclei is evaluated.

14. The cell evaluation method according to claim 1,
 wherein, in the labeling step, a chemical substance that can specifically label cell nuclei is used to label the cell nuclei;
 in the evaluating step, fragmented cell nuclei that have volumes less than a predetermined threshold are extracted from a 3D image of the fragmented cell nuclei acquired in the 3D-image creating step, and a fragmentation percentage of the cell nuclei is evaluated.

15. The cell evaluation method according to claim 1,
 wherein, in the labeling step, a chemical substance that can specifically label cell membranes is used to label the cell membranes; and
 in the evaluating step, an internal volume of cell membranes is calculated from a 3D image of the cell membranes that is acquired in the 3D-image creating step, thereby evaluating a volume of the cells.

16. The cell evaluation method according to claim 1, wherein, in the center-of-gravity determining step, the center-of-gravity position is determined on the basis of, among cross sections of a 3D image of the whole cell clump along a plurality of planes parallel to each other, a cross section of the cell clump in the plane that has the maximum cross-section area of the cell clump.

17. The cell evaluation method according to claim 1, wherein, in the center-of-gravity determining step, the center-of-gravity position of the cell clump is estimated on the basis of the distribution of components of each of the cells in the 3D image.

* * * * *